United States Patent [19]

Polk et al.

[11] Patent Number: 4,493,319
[45] Date of Patent: Jan. 15, 1985

[54] RING APPLICATOR HAVING FLOATING INNER TUBE

[75] Inventors: Todd J. Polk, Holland; Jerry Polizzi, Morrisville, both of Pa.

[73] Assignee: Cabot Medical Corporation, Langhorne, Pa.

[21] Appl. No.: 521,020

[22] Filed: Aug. 8, 1983

Related U.S. Application Data

[63] Continuation of Ser. No. 278,444, Jun. 29, 1981, abandoned.

[51] Int. Cl.³ ............................................. A61B 17/00
[52] U.S. Cl. .................................... 128/303 A; 128/6; 128/303.15; 128/326
[58] Field of Search ........... 128/303 A, 326, 6, 303.15

[56] References Cited

U.S. PATENT DOCUMENTS

| | | | |
|---|---|---|---|
| 3,989,049 | 11/1976 | Yoon | 128/303 A |
| 4,085,743 | 4/1978 | Yoon | 128/303 A |
| 4,226,239 | 10/1980 | Polk et al. | 128/303 A |
| 4,230,116 | 10/1980 | Watson | 128/303 A |
| 4,257,420 | 3/1981 | Terayama | 128/303 A |

Primary Examiner—Michael H. Thaler
Attorney, Agent, or Firm—Austin R. Miller

[57] ABSTRACT

The tubal ligation instrument of the present invention includes a structure for ligating anatomical tubes within the human or another animal body, structure for anesthetizing the anatomical tubes being ligated and structure for internally viewing the ligation procedure. An example of an anatomical tube is a Fallopian tube. The instrument further includes a structure for grasping the anatomical element. Usually the grasping structure is a rod having forceps at one end. This rod may be hollow with a valve attached in fluid communication with the rod's rearward end so that anesthesia may be caused to flow through the hollow channel in the rod. The application of anesthesia to an anatomical element is accomplished by introducing the anesthesia through the valve and into the hollow channel of the rod. Thus, a surgeon directing the forward end of the instrument to an anatomical element can apply an anesthetic agent to the anatomical element intraabdominally. In another embodiment of the present invention the hollow rod may contain lenses in its forward end and an eyepiece at its rearward end with light-carrying optical fibers running through the hollow portion of the rod to illuminate the anatomical element being ligated. Thus, a surgeon directing the forward end of the instrument to an anatomical element can view the anatomical element intraabdominally.

15 Claims, 17 Drawing Figures

RING APPLICATOR HAVING FLOATING INNER TUBE

This application is a continuation, of application Ser. No. 278,444, filed 6/29/81, now abandoned.

BACKGROUND OF THE INVENTION

The present invention relates to an elastic ring applicator for ligating anatomical elements, and more specifically relates to such an instrument which further includes a highly sensitive signaling means for alerting the surgeon when the applicator is about to deposit the elastic ring.

The applicator preferably also includes means for intraabdominally anesthetizing an anatomical element and for internally viewing the ligation procedure.

Although this instrument is particularly useful for performing female sterilization procedures involving the Fallopian tubes, it may be applied to the vas deferens in the human male, and to other anatomical structures.

Tubal ligation instruments have found world wide acceptance for a wide variety of purposes, but in particular have been used for sterilization. In the U.S. Pat. No. 3,834,392, granted to Lampman et al on Sep. 10, 1974, a laparoscope system is disclosed whereby a single unit contains the power source to provide illumination, oscillatory electrical power and $CO_2$ gas for laparoscopy. $CO_2$ gas under pressure is passed into the body through a needle. A trocar and cannula are inserted into the gas-filled abdominal cavity. A laparoscope connected to a source of illumination is inserted into the body cavity through the cannula. The Fallopian tubes are then identified and forceps are inserted through the cannula into the body cavity. The forceps are manipulated to successively close the passage through each Fallopian tube either by means of sending electrical oscillations through the forceps to simultaneously cut, seal and cauterize each tube in turn, or by means of a special type of clamp which clamps the passage shut.

U.S. Pat. No. 4,230,116 to Watson, granted Oct. 28, 1980, shows a tubal ligation instrument with anesthesia means for ligating anatomical elements such as Fallopian tubes. The utilization of anesthesia capabilities in such an instrument is advantageous since the areas being ligated are otherwise subjected to minor discomfort.

Like other tubal ligation instruments the Watson device discloses the use of an inner tube and an outer tube together with a biasing means, typically a helical compression spring, to warn the surgeon of the impending discharge of the elastic ring. Such a spring, however, is not helpful during the loading of elastic rings, particularly when spring resistance is counted upon to provide the necessary resistance for ring loading onto the inner tube.

Watson discloses that elastic rings are loaded onto the distal end of an inner tube by forcing them with a conical ring dilator. The inner tube is caused to protrude from the outer tube, a distance equal to the width(s) of the ring(s) placed on the inner tube. However, only the force of the spring causes the inner tube to protrude beyond the outer tube. Thus, after extended use of the instrument the spring sometimes weakens to such an extent that it becomes difficult or impossible to load rings onto the inner tube.

Further, the spring plays an important role in the surgeon's use of the Watson device. Upon intraabdominal insertion of the instrument, the surgeon retracts the slidable gripping means to a position of encountering the resistance of the helical spring. In this way, the surgeon is able to feel when the instrument is in proper orientation for applying anesthesia. Furthermore, the surgeon, upon encountering the resistance due to the spring, is informed by the yieldable resistance that he encounters that the elastic ring is about to be ejected from the inner tube. However, after the spring has become weakened after extended use it is capable of giving a false resistance feel which could even result in the surgeon's premature ejection of a ring.

Thirdly, the spring, with its helical shape and many crevices, presents a cleaning problem.

Another cleaning problem encountered in the Watson device concerns the slots and the closed end of the inner tube member. These slots can also become caked with dried blood, etc., hindering use of the instrument. The end can also become caked with blood, etc., resulting in premature release of the ring on subsequent operations.

A further problem with the Watson device concerns the size of the incision necessary to insert the instrument. The diameter of the outer housing tube in the Watson device is approximately one-half inch. Thus, a rather large trocar has been necessary to perform the ligation procedure. This sometimes causes serious psychological problems for the patient undergoing the ligation operation. The trauma to the patient is greater due to the incision diameter. There is also a greater chance of herniation due to the larger incision.

A further problem with the Watson device concerns the rotation of the device within the cannula. It is advantageous to rotate the device within the cannula to grasp the anatomical element at the proper location. If the device is tightly held by the cannula valve, both the device and the cannula must rotate to grasp the anatomical element in the proper location. If the incision is made as small as possible to prevent gas leakage, it becomes difficult to rotate the cannula in the incision. If the incision is enlarged to permit rotation of the cannula, there may be leakage of gas from the cavity. The alternative method of rotation, holding the cannula while the device is rotated, requires an additional pair of hands which makes use of the instrument more difficult and may result in contamination of the sterile field.

A further problem with the Watson device is the disassembly and assembly of the device during maintenance and cleaning. In order to disassemble the device, two steps must be performed; removal of the pin and unscrewing the inner tube. In order to assemble the device, five elements must be aligned; the hole in the inner member, the inner tube slot, the outer tube slot, the hole in the slidable finger grip and the pin.

OBJECTS OF THE INVENTION

It is an important object of the present invention to provide a tubal ligation instrument capable of having a smaller diameter than the instrument disclosed by Watson, thereby enabling the surgeon to use a smaller incision and a smaller trocar.

Another important object of the present invention is to enable the elimination of both the springs and the slots shown in the Watson device, thereby providing easier cleaning of the instrument, easier assembly and disassembly, easier loading and more predictable use of the instrument over an extended period of time.

It is a further object of the present invention to provide such a tubal ligation instrument which can also be used in conjunction with a number of other surgical procedures such as internal optical viewing of the operation, intraabdominal application of anesthesia to the element to be ligated, and electrosurgery.

It is a further object of the present invention to provide a ring application instrument in which two anatomical tubes are to be ligated in one surgical procedure by the application of two elastic rings, whereby only one elastic ring may be ejected at one time.

It is a further object of the present invention to provide a ring application instrument in which the elongated inner member rotates within the outer tube housing allowing the physician to easily grasp the anatomical element without rotating the cannula.

SUMMARY OF THE INVENTION

A ring application instrument in accordance with this invention includes an elongated inner member having an anatomical grasping means such as forceps at its forward end, said inner member grasping means being slidable in an inner tube which is a support means for one or more elastic rings. An outer tube is provided within which the inner tube fits in a freely slidable and rotatable manner. A manually engagable locking means enables the surgeon selectively to lock the inner tube, relative to the outer tube, in a position to accept loading of one or more elastic rings. In the form of the invention providing for the successive ejection of two or more rings, a manually engagable stop means is provided which is operative between the inner and outer tubes to prevent ejection of a second elastic ring after ejection of a first elastic ring.

The elongated inner member may, if desired, be of hollow construction to hold either an optical device for viewing the surgical procedure or for carrying anesthesia to the element to be ligated. The elongated inner member may be further adapted to be used in conjunction with an electrosurgical device.

Although specific forms of apparatus embodying the invention have been selected for illustration in the drawings, and although specific terminology will be resorted to in describing those forms in the specification which follows, their use is not intended to define or to limit the scope of the invention, which is defined in the appended claims.

DESCRIPTION OF THE PREFERRED EMBODIMENTS

Referring to the drawings, the ring applicator device of the present invention is designated as 10. Furthermore, with respect to the ring applicator 10 and/or any individual part thereof, the side or end closest to the patient shall be designated forward, and the side or end closest to the surgeon shall be designated rearward.

The ring applicator 10 consists of an outer tube 11 housing an inner tube 12. The diameters of tubes 11 and 12 are such that inner tube 12 has a close sliding fit within outer tube 11. Inner tube 12 houses an inner rod 13 having spring-like forceps 21 at its forward end. Attached to the rearward end of inner tube 12 is flange plate 30 having an additional hole 34. Inner rod 13 is adapted to fit into inner tube 12 by pressing the forceps 21 together and inserting them through the rearward end of inner tube 12. Similarly the inner tube 12 fits within outer tube 11 by sliding the forward end of inner tube 12 into the rearward end of outer tube 11.

Ring applicator 10 also includes a pistol grip handle adapted to fit in the surgeon's hand. The pistol grip handle includes a slidable (with respect to the outer tube 11) forward handle 14 and a stationary rearward handle 15. Rearward handle 15 engages rods 19 and 20 which are fixedly attached to forward handle 14. Thus, rearward handle 15 engages rod 20 in cylindrical passageway 26, and engages rod 19 in cylindrical passageway 35. The axes of rods 19 and 20 and passageways 26 and 35 are parallel so that rods 19 and 20 easily slide in rearward handle 15. Forward handle 14 and rearward handle 15 engage outer tube 11 through cylindrical passageways 24 and 25 respectively. Thus, outer tube 11, containing inner tube 12 and inner rod 13, is fed forward end first through cylindrical passageway 25 and then through cylindrical passageway 24. Flange plate 30, attached to inner tube 12, must be aligned so that hole 34 engages rod 20 attached to forward handle 14. Thus, inner tube 12 is freely slidable over that portion of rod 20 rearward of lip 37. Outer tube 11 is fixedly attached to rearward handle 15 by rings 36. Screw 32 attaches to the rearward end of rod 20, having a threaded bore 70, to accept screw 32 as shown clearly in FIG. 8. Similarly, valve 33 which is adapted to screw into the rearward end of inner rod 13 attaches inner rod 13 to flange plate 31. Thus, by threading screw 32 into the end of fixed rod 20, the inner rod 13 is fixedly attached to forward handle 14.

From the above discussion it can be seen that inner rod 13 having forceps 21 at its forward end and flange plate 31 attached to its rearward end is fixedly attached to forward handle 14. Similarly, outer tube 11 is fixedly attached to rearward handle 15. Since forward handle 14 is adapted slidably to engage rearward handle 15, the act of sliding the forward handle 14 rearwardly causes the forceps 21 to be drawn into the outer tube 11. Similarly, by sliding forward handle 14 forwardly, forceps 21 are caused to extend out of the forward end of outer tube 11.

Figures 4A, 4B:
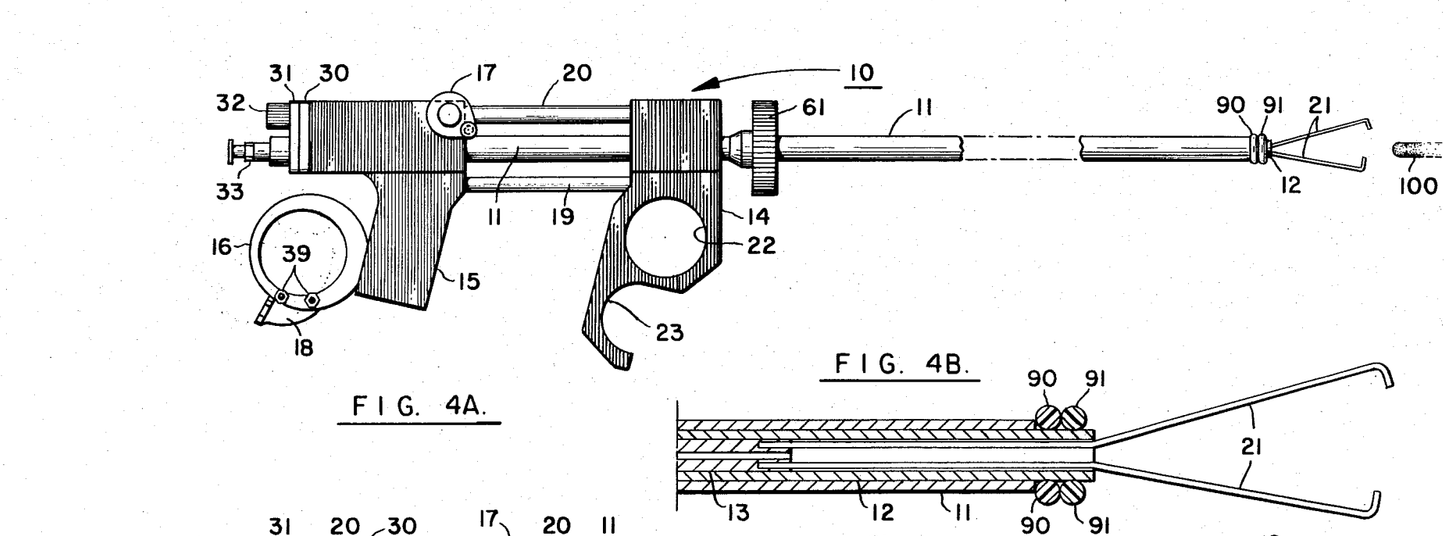
FIG. 4A is a side view of a fully loaded ring applicator with fully extended grasping means ready to grasp an anatomical element.
FIG. 4B is an enlarged, fragmentary cross-sectional view of the forward end of the ring applicator shown in FIG. 4A.
Figure 5:
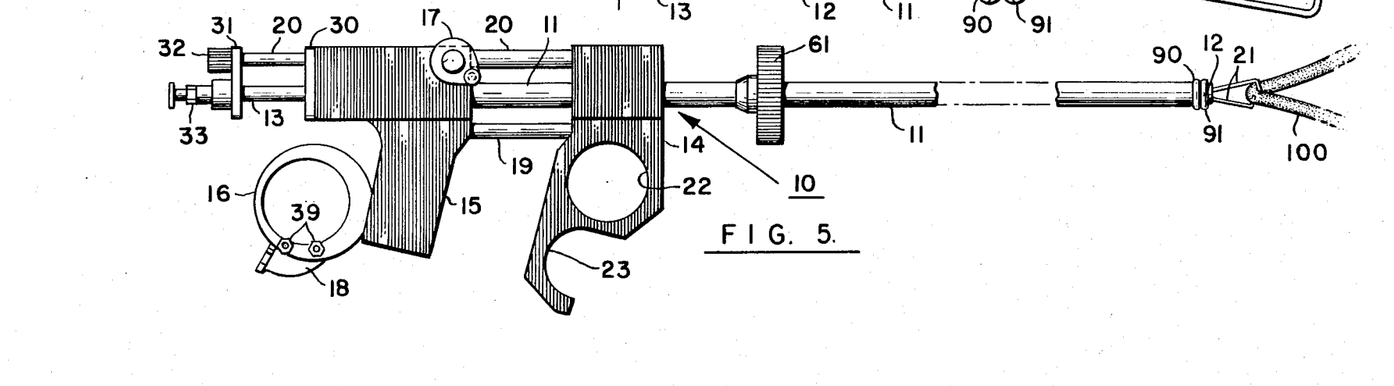
FIG. 5 is a side view of the ring applicator of FIG. 4A after it has grasped the anatomical element and is drawing it into the inner applicator tube.

The limits of the relative slidable positions of outer tube 11 and inner tube 12 are very important for purposes of ejection of elastic rings. Inner rod 13, fixedly attached to forward handle 14, by necessity has a slidable range equal to the slidable range of forward handle 14. Forward handle 14 can be slid in a rearward direction until the forward face of rearward handle 15 abuts forward handle 14 as shown in FIG. 7. Forward handle 14 also has a forward slidable limit at the point where the forward face of flange plate 31 abuts the rearward face of flange plate 30 which in turn abuts the rearward face of rearward handle 15, as shown in FIG. 4A. Similarly, inner tube 12 has a forward and rearward slidable limit. Assuming that forward handle 14 is in its most rearward slidable position, the forward slidable limit of inner tube 12 occurs when flange plate 30 encounters lip 37 of rod 20, as shown in FIG. 7. Thus, when both forward handle 14 (and thus inner rod 13) are both in their most rearward slidable positions, the forward ends of outer tube 11 and inner tube 12 are flush. As can be seen from FIG. 7, when forward handle 14 (and thus inner rod 13) are in their most rearward slidable positions, a space exists between the rearward face of rearward handle 15 and the forward face of flange plate 30. The distance separating handle 15 and flange plate 30 is approximately equal to the width of two elastic rings. This is very important in conjunction with the ring ejection procedure. By keeping inner tube 12 and flange plate 30 abutted to rearward handle 15, forward handle 14 may be slid forwardly until flange plate 31 abuts flange plate 30. At this point, the forward end of inner tube 12 protrudes beyond the forward end of outer tube 11 a distance approximately equal to the width of two rings and the forceps 21 protrude beyond inner tube 12. With flange plate 30 abutted to rearward handle 15, forward handle 14 may be slid rearwardly until lip 37 of rod 20 encounters flange plate 30. With further rearward movement of forward handle 14, inner tube 12 will slide rearwardly in relation to outer tube 11. This slidable span will result in ring ejection.

Forward handle 14 and rearward handle 15 are shown in the drawings as having a shape substantially like a pistol grip. However, the rotatable ring 16 is adapted for engagement by the surgeon's thumb. The ring 16 is rotatable on rearward handle 15 and attached thereto by a screw 38. The screw 38 is unthreaded in the rearward handle 15 and is only screwed into the ring 16; thus it is rotatable. The rotatable ring 16 provides a comfortable means of grasping the ring applicator 10, whether the surgeon be left or right-handed. Since the ring 16 is rotatable, it can move about to fit comfortably on either a right-hand or left-hand thumb. While forward handle 14, rearward handle 15 and rotatable ring 16 are shown as being in a pistol-grip shape, it should, nevertheless, be appreciated that the handles can have other conventional shapes. For example, the ring 16 can be of a generally U-shaped or generally square-shaped configurations, or others.

Figure 1:
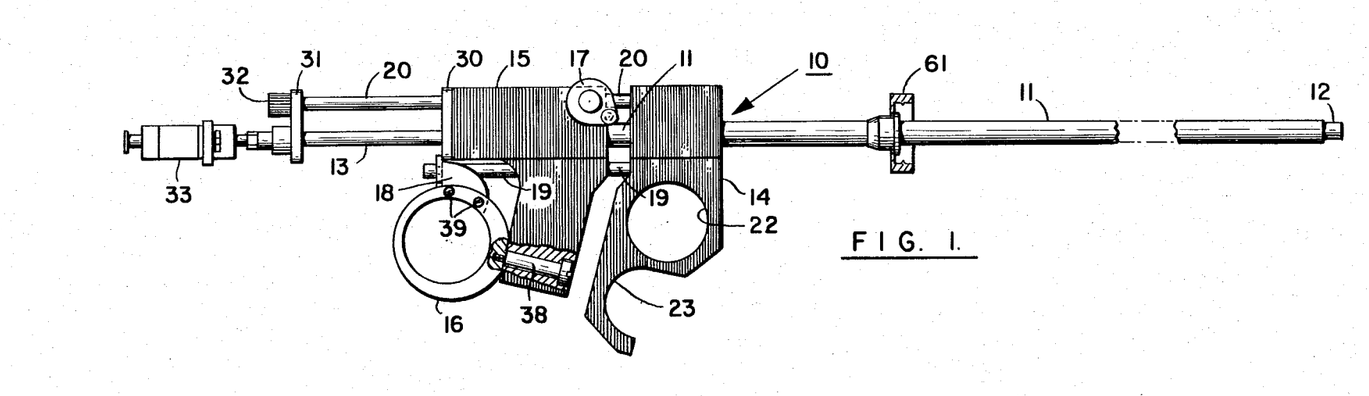
FIG. 1 is a side elevation of a ring applicator comprising one specific embodiment of the present invention.

An important advance over the ligation instruments of the prior art is the latch 18 attached to ring 16 by screws 39. Referring to FIG. 1, ring applicator 10 is shown in a locked position ready to accept loading of elastic rings. Ring applicator 10 is locked into the loading position by sliding flange plate 30 forward until it abuts the rearward face of rearward handle 15. Ring 16 is then rotated until latch 18 engages notch 60 in rod 19. While latch 18 engages rod 19, flange plate 30 is held flush against the rearward face of rearward handle 15. Thus, while the ring applicator 10 is in a locked position, inner tube 12 is unable to slide with respect to outer tube 11. Furthermore, while in this locked position, inner tube 12 extends beyond the forward end of outer tube 11 a distance slightly greater than the width of two elastic rings. With the ring applicator 10 in a locked position it is now ready for ring loading.

Figure 3A:
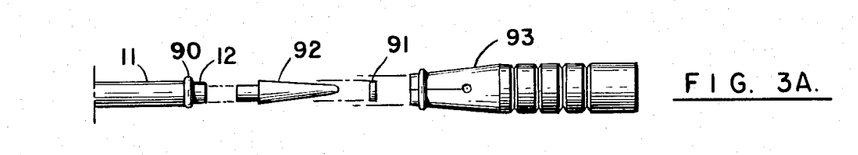
FIGS. 3A, 3B and 3C are side views of the forward end of the ring applicator of FIGS. 1 and 2, illustrating a preferred procedure for loading the elastic rings.
Figure 3B:
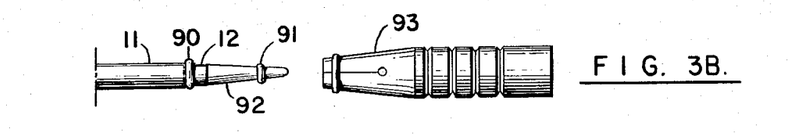
Figure 3C:
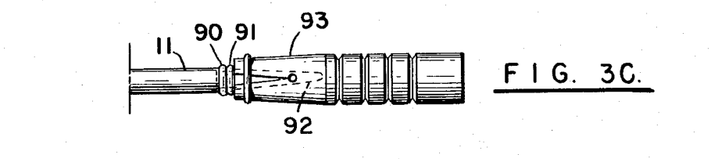

FIGS. 3A, 3B and 3C illustrate sequentially the ring loading operation. Ring loading (of itself) is known in the art and is described herein only for purposes of illustration.

Cone 92 is adapted to fit into the forward end of inner tube 12. An elastic ring 90 is then placed on the tip of cone 92. Elastic ring 90 is then forced down cone 92 by ring sliding device 93. The first elastic ring loaded, ring 90, is slid over inner tube 12 until it abuts the forward end of outer tube 11. The second ring 91 is slid over inner tube 12 until it abuts the first ring 90. Many operations, such as sterilization of females through ligation of Fallopian tubes, require the use of two elastic rings in order to ligate two tubes. Thus, by loading two elastic rings onto ring applicator 10 the surgeon can perform the entire ligation operation without having to withdraw and reload the ring applicator 10 during surgery.

Referring to FIG. 4A, a fully loaded ring applicator 10 is shown with fully extended forceps 21 ready to grasp anatomical tube 100. As can be seen from the drawing, forward handle 14 is in its most forward slidable position. Thus, outer tube 11 and inner tube 12 are also in their most rearward slidable positions. Hence, the spring-like forceps 21 are exposed and opened.

FIG. 4B is an enlarged cross-sectional view of the forward end of ring applicator 10 shown in FIG. 4A. The open position of the forceps 21 is clearly shown as well as the respective positions of elastic rings 90 and 91.

Once the anatomical tube is positioned between the forceps 21, the surgeon closes the forceps by sliding forward handle 14 in a rearward direction. By so doing, inner rod 13 is slid rearwardly with respect to inner tube 12 and outer tube 11 thereby closing the forceps 21 around anatomical tube 100. As forward handle 14 is slid even further rearwardly, anatomical tube 100 is drawn inside inner tube 12.

It is important to have pin 17 rotated into a position between the forward side of rearward handle 15 and the rearward side of forward handle 14, prior to and during the ligation with the first ring to be ejected. By making the diameter of rotatable pin 17 approximately equal to the width of elastic ring 90 the surgeon is assured that only the most forward positioned elastic ring 91 will be ejected onto anatomical tube 100 and that elastic ring 90 will remain in place. Pin 17 is in a position between handles 14 and 15 during ligation of the first anatomical tube 100 and ejection of the first ring 91 as shown in FIGS. 4A, 4B, 5 and 6A.

Figure 6A:
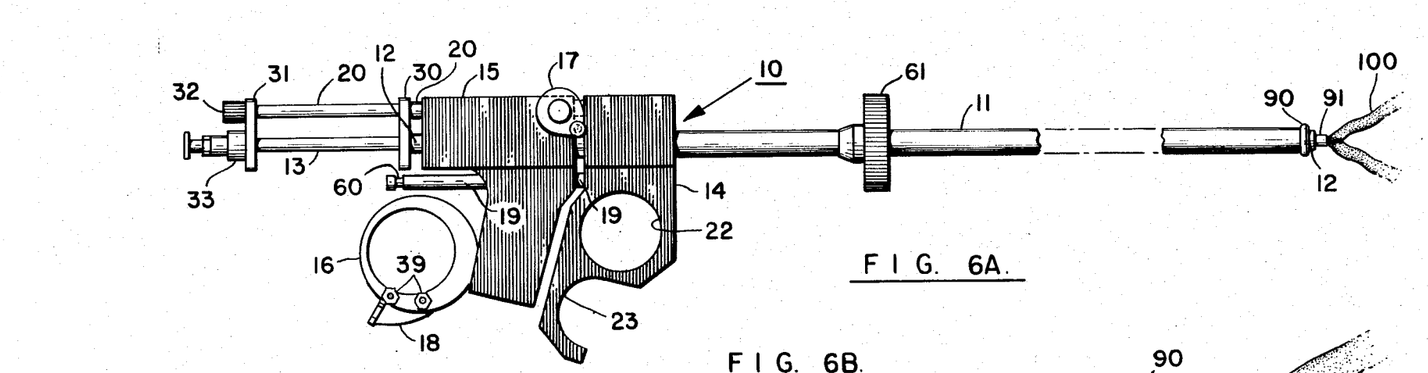
FIGS. 6A, 6B and 7 are cross-sectional and side views illustrating the operation of one form of ring applicator device in accordance with the present invention.
Figures 6B, 7:
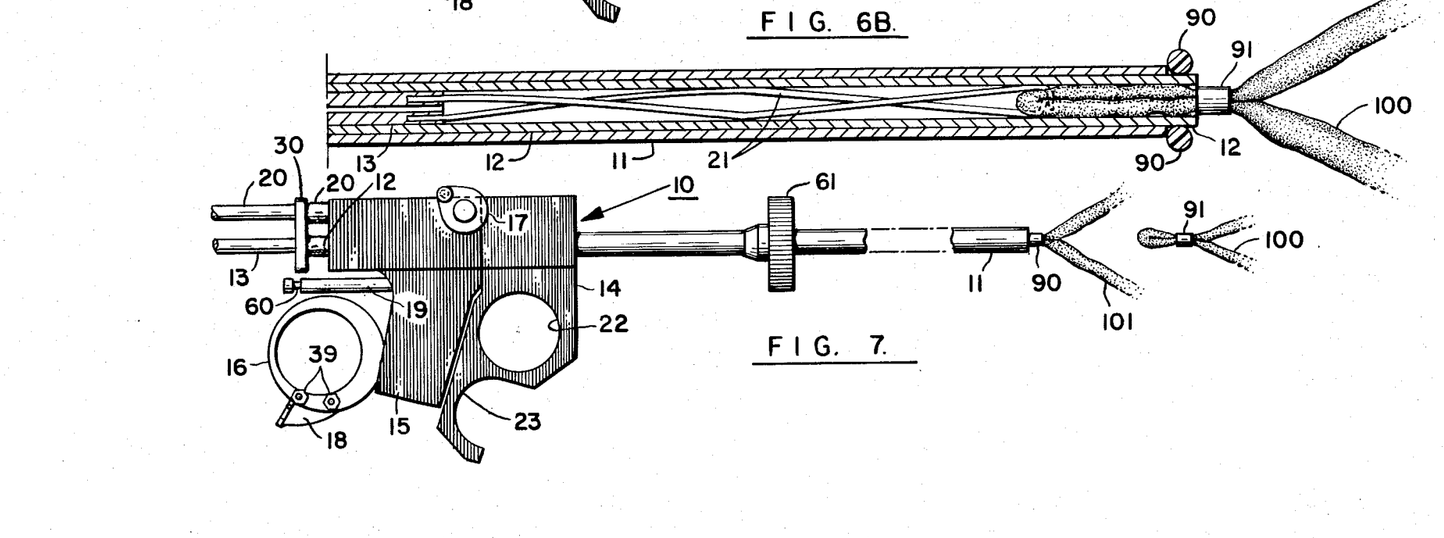

Referring to FIG. 6A, the ring applicator 10 is shown immediately after the first ring 91 has been ejected to effect ligation of anatomical tube 100. As can be seen, rotatable pin 17 has been rotated into a position between the forward handle 14 and the rearward handle 15 thereby preventing further sliding of outer tube 11 with respect to inner tube 12 and thereby preventing the ejection of the second elastic ring 90.

FIG. 6B is an enlarged cross-sectional view of the forward end of ring applicator 10 of FIG. 6A. Anatomical tube 100 is grasped by forceps 21 and pulled inside inner tube 12 as inner rod 13 is slid rearwardly with respect to inner tube 12 and outer tube 11. Furthermore, inner tube 12 is slid rearwardly a distance approximately equal to the width of one elastic ring 91 with respect to outer tube 11 thereby causing elastic ring 91 to be pushed off the end of the inner tube 12. This sliding movement is accomplished against the friction of the elastic rings on the inner tube 12, signaling to the surgeon the impending discharge of the elastic ring 91. Upon ejection of elastic ring 91 the surgeon feels a slight snap caused by the sudden ejection of ring 91. In this way, the surgeon can feel when the ligation of anatomical tube 100 is about to occur and when it has been accomplished.

To release anatomical tube 100 the surgeon merely slides the forward handle 14 in a forward direction thereby causing the forceps 21 to protrude from the end of inner tube 12 thereby allowing the (self-opening) forceps 21 to spring open and release anatomical tube 100.

The same basic sequence of events is then undertaken with respect to the second anatomical tube 101 to be ligated. The only difference between the first ligation and the second ligation is that to perform the second ligation the rotatable pin 17 must be rotated out of its position between forward handle 14 and rearward handle 15 in order that inner tube 12 can be slid rearwardly to a position where the forward end of outer tube 11 is flush with the forward end of inner tube 12. This rearward sliding of inner tube 12 with respect to outer tube 11 pushes off the remaining elastic ring 90 (with the same "signals" to the surgeon) into a position around anatomical tube 101 thereby affecting ligation of anatomical tube 101. Anatomical tube 101 is then released by sliding forward handle 14 in a forward direction to expose and spring open forceps 21.

Figure 8:
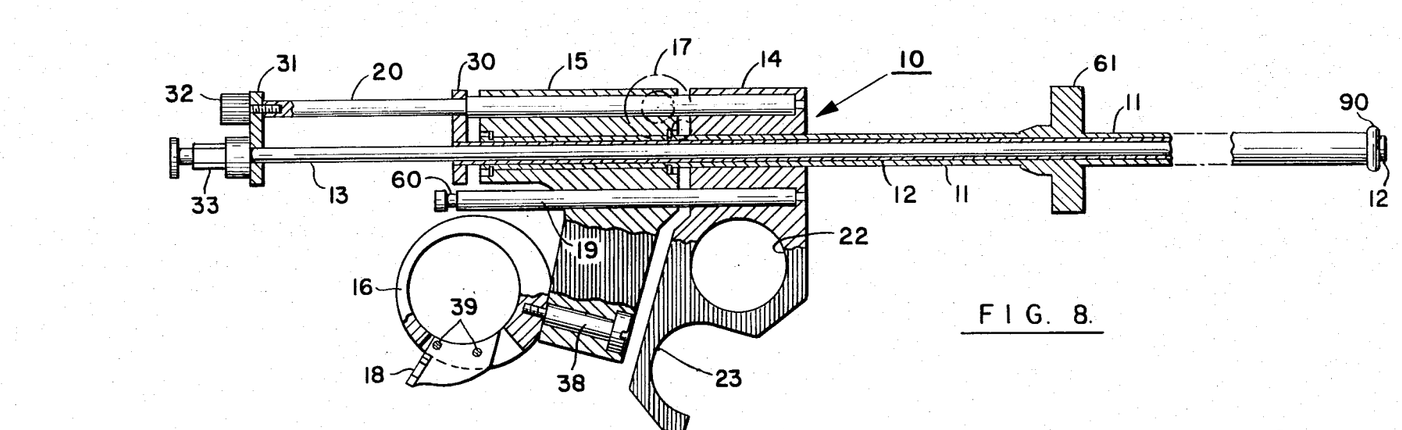
FIG. 8 is a side view of the ring applicator, with certain portions cut away and shown in cross section in order to reveal important details.
Figure 9:
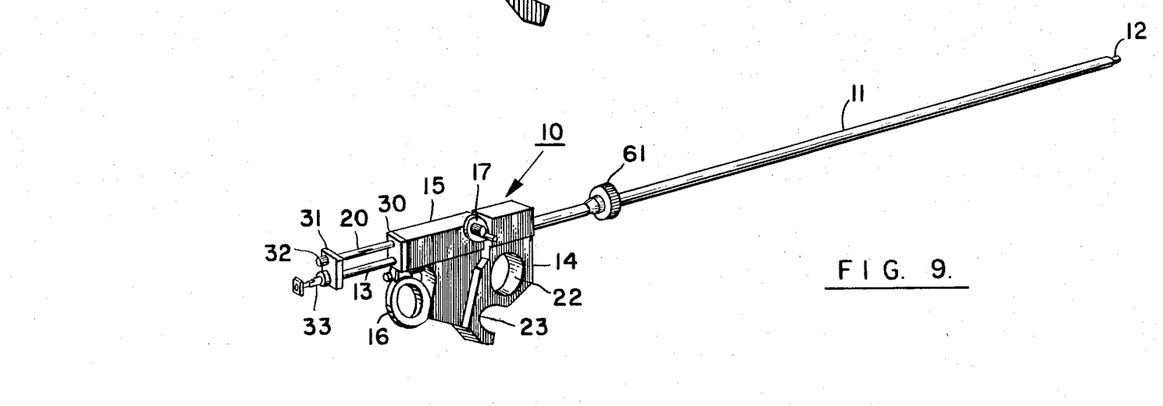
FIG. 9 is a perspective view of the ring applicator in a locked position.

Referring to FIG. 8, the absence of any springs or slots in ring applicator 10 is clearly shown. Furthermore, the close sliding fit between tubes 11 and 12 and inner rod 13 is shown. These smooth surfaces present no crevices where dried blood or other debris can accumulate and interfere with the smooth operation of the instrument, or with its subsequent cleaning. The close sliding fit also prevents the escape of gas without requiring use of additional seals.

Figure 2:
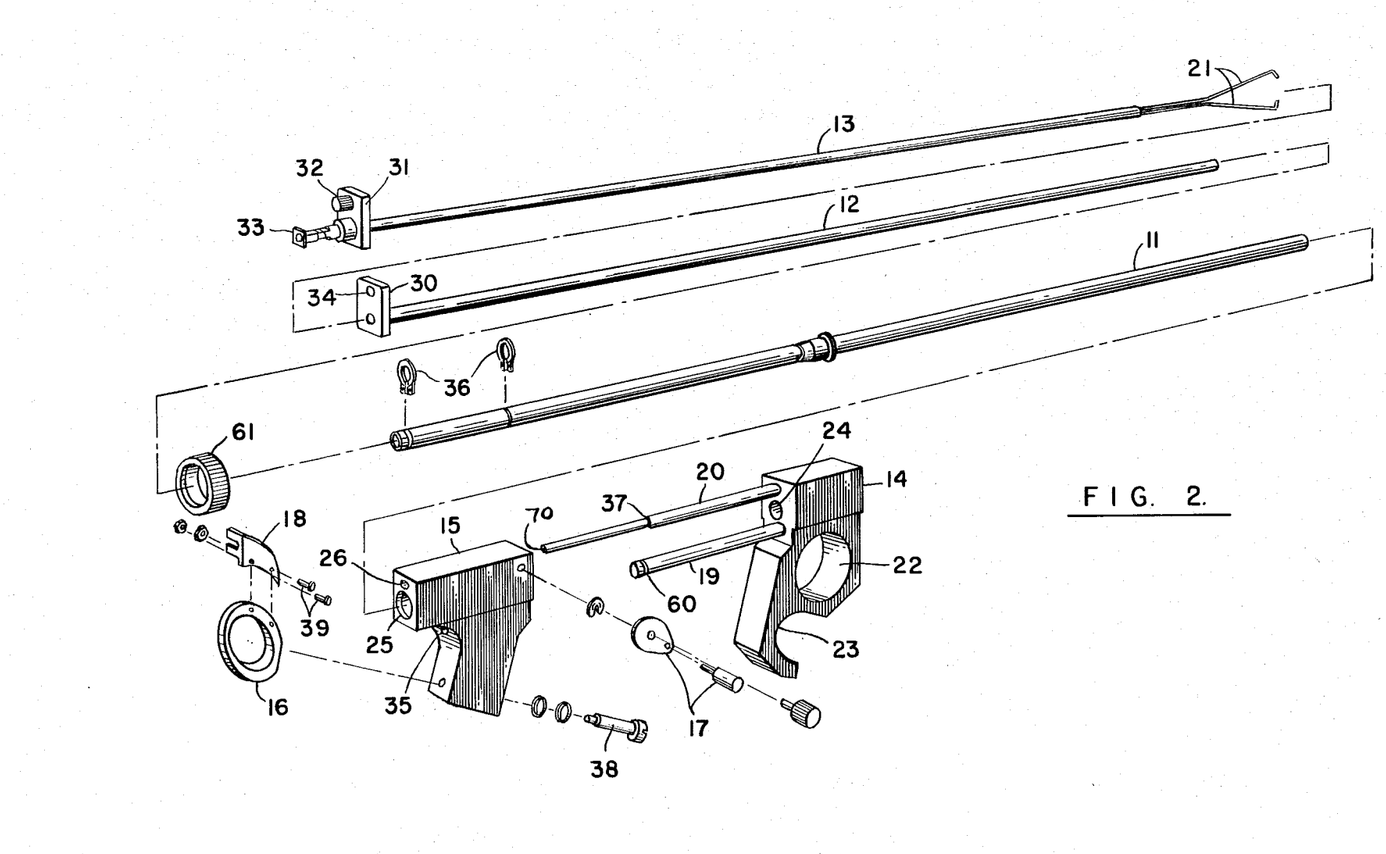
FIG. 2 is an exploded view of the ring applicator of FIG. 1.

One of the major advantages of the ring applicator 10 of this invention is that the entire device is easily disassembled for cleaning, maintenance, sterilization or replacement. As viewed in FIG. 2, the separate parts contain mostly smooth, open and easily accessible surfaces. Although it is preferred to clean and sterilize the parts separately, they can be cleaned separately, and then reassembled and sterilized as one unit.

In disassembling the ring applicator 10, screw 32 is unscrewed. This allows removal of both inner rod 13 and inner tube 12. Thus, the entire ring applicator 10 can be assembled and disassembled in a matter of seconds into three conponent parts, namely, an inner rod assembly, an inner tube assembly and an outer tube with attached pistol grip handles.

Figure 10:
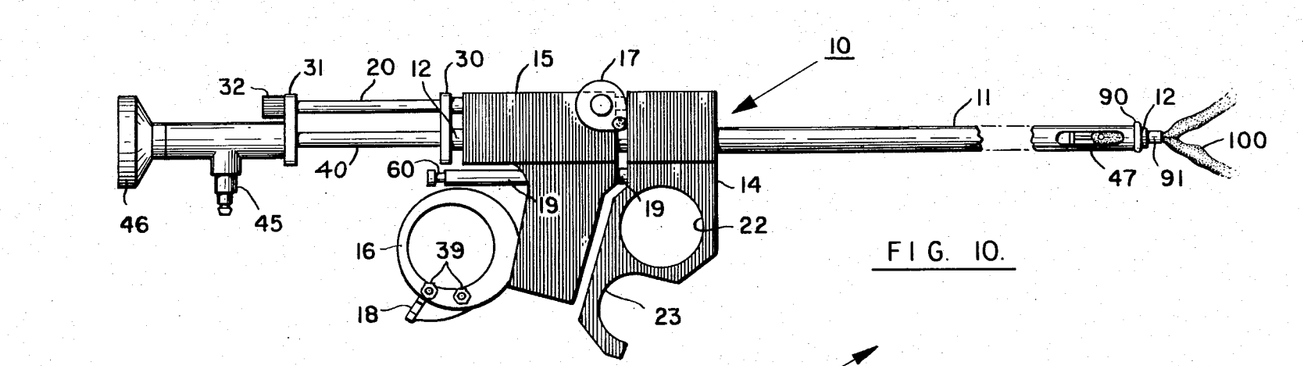
FIGS. 10, 11A and 11B are side (enlarged), and cross-sectional views, respectively, of a ring applicator utilizing an optic viewing system with a fiber optic illumination system in accordance with this invention.
Figures 11A, 11B, 12:
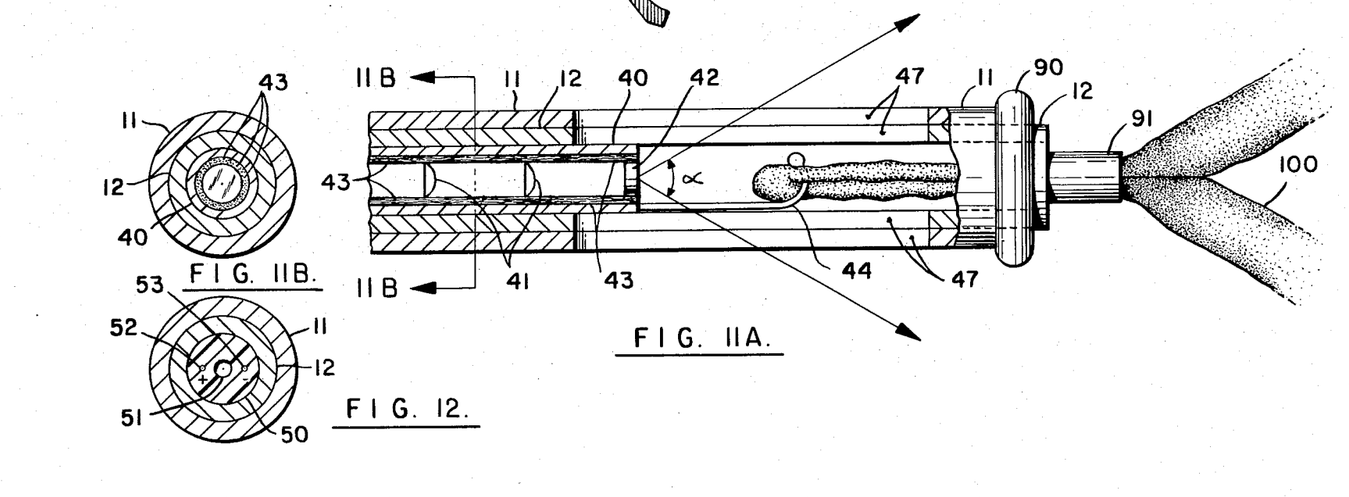
FIG. 12 is a cross-sectional view of a modified form of applicator, showing an apparatus for performing electrosurgery in accordance with the present invention.

Such easy assembly and disassembly of the ring applicator 10 permits fast substitution of parts for different embodiments of the present invention. One such preferred embodiment is shown in FIGS. 10, 11A and 11B. In this embodiment, the inner rod 13 having two spring-like forceps 21 is replaced with a hollow rod 40 containing lenses 41, window 42 and light-carrying optical fibers 43. Attached to the forward end of hollow rod 40 is a single tong 44 used to hook the anatomical tube 100. Tong 44 has a spherical tip, to avoid cutting or puncturing the anatomical tube 100. The optical fibers run along the length of hollow rod 40 and parallel to its axis. The positioning of the optical fibers 43 around the interior surface of hollow rod 40 is shown in FIG. 11B. At the rearward end of hollow rod 40 is attached a fiber optic connector 45. Fiber optic connector 45 is well known in the art and forms no part of the present invention other than to illustrate the use of the novel forward tip configuration of the present fiber optic embodiment. A light-emitting source is operationally connected to fiber optic connector 45 which in turn directs illumination through the individual optical fibers 43 running through hollow rod 40. In this way, illumination is provided enabling the surgeon to view the anatomical tube to be ligated. Generally the surgeon views the procedure through eyepiece 46.

It should be noted that the field of vision for the narrow hollow tube 40 and lenses 41 is inherently limited to the available angle $\alpha$. However, when inner tube 12 and outer tube 11 are composed of metal or other opaque materials, the field of view which the surgeon is afforded is considerably narrowed when the inner rod 40 is inside inner tube 12. This "tunnel vision" effect can be lessened by providing windows 47 in the sides of tubes 11 and 12. One window 47 is clearly shown in FIG. 10. A second window 47 is on the opposite side of tubes 11 and 12. These windows 47 give the surgeon a fuller field of vision and allow him to view the periphery around the anatomical element 100 being ligated.

In addition, the ring applicator 10 of the present invention may be used in conjunction with other optical viewing devices. One such device known to the prior art slidably fits over outer tube 11 and is fastened to ring applicator 10 by threadably engaging fastener 61, A further embodiment of the present invention is illustrated in FIG. 12. In this embodiment the ring applicator 10 is combined with an electrosurgical device. To convert the standard ring applicator 10 to a combined ring applicator and electrosurgical device, inner rod 13 is replaced with a hollow rod 50 composed of a nonconductor (preferably of nylon) carrying electrical wires 52 and 53. Rod 50 is hollow with an inner channel 51 which can be used to convey anesthesia to the ligation area. Furthermore, wires 52 and 53 run within the walls of rod 50. Because the material of rod 50 is an insulator there is no danger of short-circuiting between wires 52 and 53. Wires 52 and 53 are connected to an electrical supply at the rearward end of hollow rod 50. At the forward end of rod 50 the wires are connected to ordinary spring-like forceps 21 as shown in FIG. 1. The inner tube 12 in this configuration is made of an insulating material such as teflon.

This mode of using the present invention is helpful in an operation where the surgeon first discovers upon inserting the instrument that the anatomical tubes, due to disease or some other condition, do not have the inherent structural integrity to support an elastic ring. In such a case, the electrosurgical device is a desirable backup system to simultaneously cut, seal and cauterize each anatomical tube.

Both hollow rod 40 and rod 50 have the same dimensions as inner rod 13. Thus, both the optical viewing and electrosurgical embodiments of the present invention fit equally well with the ring applicator 10 described herein and in the drawings. This means that the diameter of outer tube 11, being typically and desirably approximately one-fourth inch, determines the size of the incision made by the surgeon's trocar in the ligation procedure. This is remarkable indeed when compared with available prior art devices.

Although this invention has been described in connection with specific forms thereof, it will be appreciated by those skilled in the art that a wide variety of equivalents may be substituted for those specific elements and steps of operation shown and described herein, that certain features may be used independently of other features, and that parts may be reversed, all without departing from the spirit and scope of this invention as defined in the appended claims.

We claim:

1. In a surgical ligating instrument for tubal ligation by the application of an elastic ring to an anatomical tubular member, the combination which comprises:
 a. an elongated inner member having a forward and a rearward end and having a grasping means at its forward end constructed and arranged for grasping said anatomical tubular member to be ligated;
 b. handle-less, tube means freely slidably carried upon said inner member (a) with close sliding fit therebetween, said tube means (b) having an outer surface adjacent its forward end over which at least one elastic ring is adapted to fit in a tensioned condition;
 said tube means (b) and all portions of the instrument fixedly attached thereto being free of any slot;
 c. a slotless outer tube surrounding and having a close sliding fit around the tube means (b) so as to substantially isolate the tube means (b) from the anatomical environment;
 d. releasable securing means for securing said tube means (b) in a forward position relative to said outer tube (c);
 e. means, operated by sliding together forward and rearward handles, the forward handle being fixedly attached to the inner member (a), the rearward handle being attached to the outer tube (c), to retract said member (a) relative to said tube means (b) to draw said anatomical tubular member rearwardly into said tube means (b);
 f. means operated by further sliding together the two handles to retract said tube means (b) relative to said outer tube (c) to eject said elastic ring from the surface of said tube means (b) while said anatomical tube to be ligated extends into said tube means (b), thereby displacing said elastic ring to a position surrounding said anatomical tubular member and effecting tubal ligation thereof; and
 g. manually engagable stop means positioned to prevent further retraction of said tube means (b) relative to said outer tube (c) after said elastic ring has been ejected in response to said retraction of said tube means (b), wherein the instrument is free of any spring.

2. In a surgical ligating instrument for tubal ligation by the application of an elastic ring to an anatomical tubular member, the combination which comprises:
 a. an elongated inner member having a forward and a rearward end and having a grasping means at its forward end constructed and arranged for grasping said anatomical tubular member to be ligated;
 b. handle-less tube means freely slidably carried upon said inner member (a) with close sliding fit therebetween, said tube means (b) having an outer surface adjacent its forward end over which at least one elastic ring is adapted to fit in a tensioned condition;
 c. a slotless outer tube substantially surrounding and having a close sliding fit around the tube means (b) so as to substantially isolate the tube means (b) from the anatomical environment;
 d. releasable securing means for securing said tube means (b) in a forward position relative to said outer tube (c);
 e. means, operated by sliding together forward and rearward handles the forward handle including a curved portion adapted to contact a surgeon's index finger the forward handle being fixedly attached to the inner member (a) the rearward handle including a rotatable ring adapted for insertion of a surgeon's thumb, the rotatable ring having a manually engagable latching means attached thereto for engaging a fixed rod attached to the forward handle the rearward handle being attached to the outer tube (c), to retract said member (a) relative to said tube means (b) to draw said anatomical tubular member rearwardly into said tube means (b);
 f. means operated by further sliding together the forward and rearward handles to retract said tube means (b) relative to said outer tube (c) to eject said elastic ring from the surface of said tube means (b) while said anatomical tube to be ligated extends into said tube means (b), thereby displacing said elastic ring to a position surrounding said anatomical tubular member and effecting tubal ligation thereof; and
 g. manually engagable stop means positioned to prevent further retraction of said tube means (b) relative to said outer tube (c) after said elastic ring has been ejected in response to said retraction of said tube means (b).

3. The instrument defined in claim 2, wherein the forward most handle is attached to the rearward portion of said inner member (a).

4. The instrument defined in claim 2, wherein the rearward most handle is attached to a rearward portion of said outer tube (c).

5. The instrument defined in claim 2, wherein said rearward handle slidably engages said fixed rod.

6. The instrument defined in claim 5, wherein said latching means engages inner tube means (b) to lock said inner tube means (b) in a forward slidable position relative to outer tube (c).

7. The instrument defined in claim 2, wherein the forward end of inner tube means (b) extends beyond the forward end of outer tube (g) by the width of two elastic rings when the instrument is in a locked position.

8. The instrument defined in claim 2, wherein said stop means comprises a rotatable pin member having a diameter approximately equal to the width of an elastic ring and is rotatable into and out of a position between the forward end of the rearward handle and the rearward end of the forward handle.

9. The instrument defined in claim 2, wherein said inner member (a) is an elongated rod having forceps having a pair of spring-like legs at its forward end adapted for grasping said anatomical tube to be ligated.

10. The instrument defined in claim 2, wherein said inner member (a) is a hollow rod having forceps at its forward end and a fluid valve attached in fluid communication to its rearward end to control the flow of anesthetic agent through the hollow portion of the rod.

11. The instrument defined in claim 2, wherein said instrument is combined with and connected to an optical viewing device and wherein said optical viewing device includes a bore which has an inner diameter which forms a close sliding fit with the outer diameter of said outer tube (c).

12. The instrument defined in claim 11, wherein said insulating material is nylon.

13. The instrument defined in claim 2, wherein said inner member (a) is a hollow rod composed of an insulating material with electrical conduit means contained within said rod and connected to an electrode at the forward end of said rod and to an electrical power supply.

14. The instrument defined in claim 2, wherein said inner member (a) is a hollow rod containing both light carrying optical fibers and lenses enabling the surgeon to view the operation by looking through the hollow rod.

15. The instrument defined in claim 14, wherein said tube means (b) has an opening cut in its walls in proximity to its forward end, enabling the surgeon to see the periphery of the forward end of the instrument.

* * * * *